(12) United States Patent

Muraoka et al.

(10) Patent No.: US 7,067,528 B2
(45) Date of Patent: Jun. 27, 2006

(54) 1, 2-DIHYDRO-2-OXO-1, 8-NAPHTHYRIDINE DERIVATIVE

(75) Inventors: Masami Muraoka, Suita (JP); Satoshi Ohnuma, Nishinomiya (JP); Hitoshi Ban, Nishinomiya (JP)

(73) Assignee: Sumitomo Pharmaceuticals Co., Ltd., Osaka (JP)

( * ) Notice: Subject to any disclaimer, the term of this patent is extended or adjusted under 35 U.S.C. 154(b) by 360 days.

(21) Appl. No.: 10/474,725

(22) PCT Filed: Aug. 14, 2002

(86) PCT No.: PCT/JP02/08266

§ 371 (c)(1),
(2), (4) Date: Oct. 14, 2003

(87) PCT Pub. No.: WO03/018581

PCT Pub. Date: Mar. 6, 2003

(65) Prior Publication Data
US 2004/0116463 A1 Jun. 17, 2004

(30) Foreign Application Priority Data
Aug. 23, 2001 (JP) ........................... 2001-252673

(51) Int. Cl.
*A61K 31/44* (2006.01)

(52) U.S. Cl. .................... 514/300; 546/122
(58) Field of Classification Search ........... 546/122; 514/300
See application file for complete search history.

(56) References Cited

U.S. PATENT DOCUMENTS 5,843,957 A    12/1998  Muraoka et al. ........... 514/300

6,420,381 B1   7/2002  Muraoka et al. ........... 514/300

FOREIGN PATENT DOCUMENTS

| EP | 0842933 A1 | 5/1998 |
| EP | 0947515 A1 | 10/1999 |
| EP | 1 086 948 A1 | 3/2001 |
| EP | 1104763 A1 | 6/2001 |

*Primary Examiner*—Amelia A. Owens
(74) *Attorney, Agent, or Firm*—Birch, Stewart, Kolasch & Birch, LLP

(57) ABSTRACT

Hydrates of N-[1-butyl-4-[3-[3-(hydroxy)propoxy]-phenyl]-1,2-dihydro-2-oxo-1,8-naphthyridin-3-yl]-N'-(2,6-diisopropyl-4-aminophenyl)urea hydrochloride of the formula:

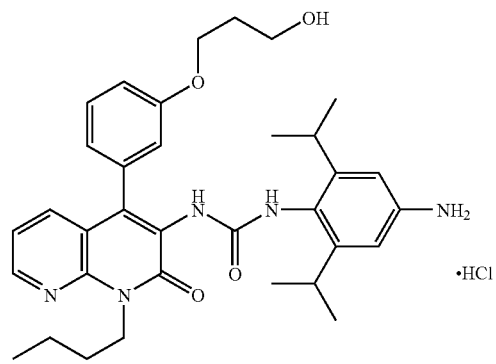

are quite excellent in stability than amorphous one and are more preferable for medicaments.

5 Claims, 1 Drawing Sheet

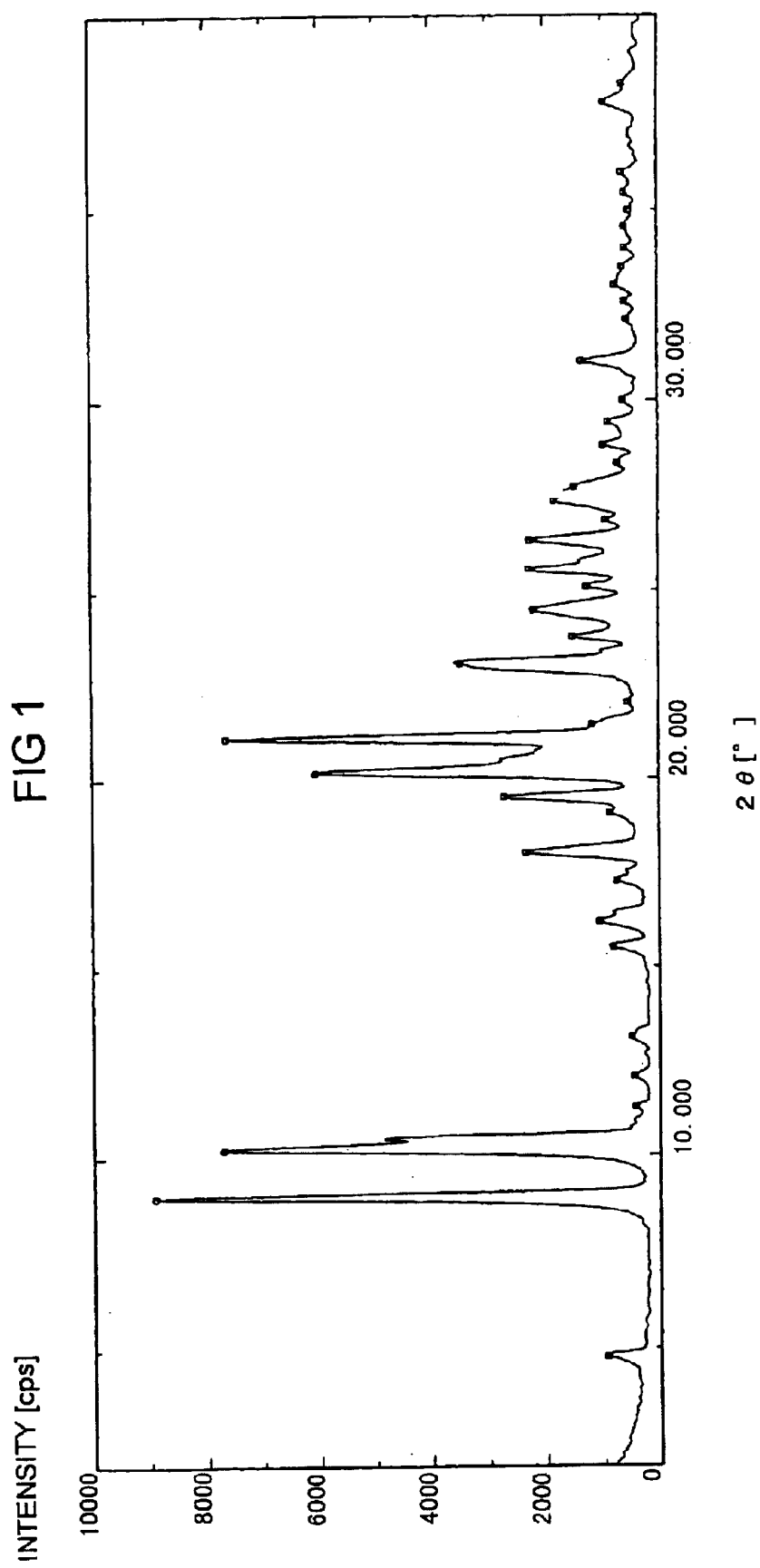

1, 2-DIHYDRO-2-OXO-1, 8-NAPHTHYRIDINE DERIVATIVE

This application is the national phase under 35 U.S.C. §371 of PCT International Application No. PCT/JP02/08266 which has an International filing date of Aug. 14, 2002, which designated the United States of America. This application claims priority under 35 U.S.C. §119(a)–(d) of JP 2001-252673, filed in Japan on Aug. 23, 2001.

TECHNICAL FIELD

The present invention relates to a hydrate of 1,2-dihydro-2-oxo-1,8-naphthyridine derivative, which exhibits acyl-CoA: cholesterol acyl transferase (ACAT) inhibitory activity, and is useful as an agent for treatment of hyperlipidemia and atherosclerosis.

BACKGROUND ART

WP 00/09505 discloses a colorless amorphous product of N-[1-butyl-4-[3-[3-(hydroxy)propoxy]phenyl]-1,2-dihydro-2-oxo-1,8-naphthyridin-3-yl]-N'-(2,6-diisopropyl-4-aminophenyl)urea hydrochloride having an acyl-CoA: cholesterol acyl transferase (ACAT) inhibitory activity and being useful as an agent for treatment of hyperlipidemia and/or atherosclerosis.

DISCLOSURE OF INVENTION

An object of the present invention is to provide a stable hydrate of N-[1-butyl-4-[3-[3-(hydroxy)propoxy]-phenyl]-1,2-dihydro-2-oxo-1,8-naphthyridin-3-yl]-N+-(2,6-diisopropyl-4-aminophenyl)urea or a pharmaceutically acceptable salt thereof, which has an ACAT inhibitory activity and is useful as an agent for treatment of hyperlipidemia and atherosclerosis.

The present inventors have intensively studied in order to solve the above problem, and have found that N-[1-butyl-4-[3-[3-(hydroxy)propoxy]phenyl]-1,2-dihydro-2-oxo-1,8-naphthyridin-3-yl]-N'-(2,6-diisopropyl-4-aminophenyl)-urea hydrochloride monohydrate can be obtained in the form of a stable crystal, and have accomplished the present invention. Thus, the present invention provides the embodiments as shown below.

[1] A hydrate of N-[1-butyl-4-[3-[3-(hydroxy)propoxy]-phenyl]-1,2-dihydro-2-oxo-1,8-naphthyridin-3-yl]-N'-(2,6-diisopropyl-4-aminophenyl)urea hydrochloride of the formula:

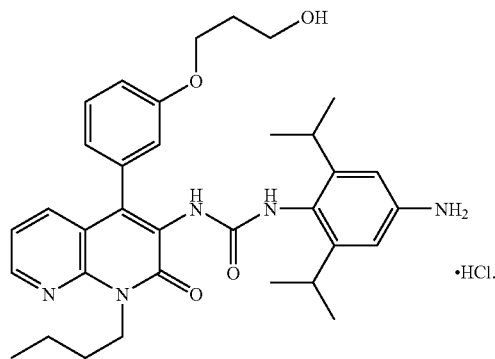

[2] The compound according to the above [1], which is a monohydrate.
[3] The compound according to the above [2], which has main peaks at the diffraction angles (2θ) of 8.8°, 10.1°, 20.1° and 21.0° in the powder X-ray diffraction pattern.
[4] A medicament comprising the compound as set forth in any one of the above [1] to [3].
[5] An acyl-CoA: cholesterol acyl transferase (ACAT) inhibitor, which comprises as an active ingredient the compound as set forth in any one of the above [1] to [3].
[6] An agent for treatment of hyperlipidemia or atherosclerosis, which comprises as an active ingredient the compound as set forth in any one of the above [1] to [3].

In the powder X-ray diffraction pattern of the crystals of the present description, the values of the diffraction angle have the standard accuracy such as about ±0.1°.

N-[1-Butyl-4-[3-[3-(hydroxy)propoxy]phenyl]-1,2-dihydro-2-oxo-1,8-naphthyridin-3-yl]-N'-(2,6-diisopropyl-4-aminophenyl)urea hydrochloride may be prepared by the method disclosed in WO 00/09505, or a modified method thereof. The monohydrate thereof may be prepared by warming said hydrochloride in an aqueous hydrophilic solvent at a temperature of from 0° C. to a boiling point of the solvent used. In addition, the monohydrate may also be prepared by recrystallizing said hydrochloride in an aqueous hydrophilic solvent. The hydrophilic solvent includes alcohols such as methanol, ethanol, isopropanol, etc. Preferable hydrophilic solvent is methanol. The moisture content in the hydrophilic solvent is in the range of 0.5% (v/v) to 50% (v/v), more preferably in the range of 1% (v/v) to 20% (v/v).

The present compound may be administered either parenterally or orally when used as the above-mentioned medicaments. That is, the present compound may be formulated into liquid preparations such as suspensions, etc., and can be administered in the form of an injection, and if necessary, buffering agents, solubilizers and isotonic agents may be added thereto. The present compound may also be administered in rectal route in the form of a suppository. The present compound may also be administered orally in a conventional dosage form such as tablets, capsules, syrups, and suspension. These formulations can be prepared by mixing an active ingredient with conventional carriers or diluents, binding agents or stabilizers in a usual manner.

The dosage and the frequency of administration of the present compound may vary according to the conditions, ages, weights of the patients and the dosage form, etc., but the present compound may usually be administered orally in a dose of 1 to 500 mg per day in adult, once a day, or divided into 2–4 dosage units.

BRIEF DESCRIPTION OF DRAWING

FIG. 1 is a powder X-ray diffraction pattern of N-[1-butyl-4-[3-[3-(hydroxy)propoxy]phenyl]-1,2-dihydro-2-oxo-1,8-naphthyridin-3-yl]-N'-(2,6-diisopropyl-4-aminophenyl)-urea hydrochloride monohydrate obtained in Example 1. The abscissa axis indicates a diffraction angle (2θ) [°], and the vertical axis indicates an intensity [cps] (count per second).

EXAMPLES

The present invention is illustrated in more detail by Example, but should not be construed to be limited thereto.

Example 1

N-[1-butyl-4-[3-[3-(hydroxy)propoxy]phenyl]-1,2-dihydro-2-oxo-1,8-naphthyridin-3-yl]-N'-(2,6-diisopropyl-4-aminophenyl)urea hydrochloride monohydrate A suspension of an amorphous solid of N-[1-butyl-4-[3-[3-(hydroxy)propoxy]phenyl]-1,2-dihydro-2-oxo-1,8-naphthyridin-3-yl]-N'-(2,6-diisopropyl-4-aminophenyl)urea hydrochloride (125 g) in methanol (375 ml) was stirred with heating at about 60° C. to dissolve the solid. Water (3.7 ml)

was added thereto, and the mixture was stirred for 15 minutes, and filtered while the mixture was hot. The filtrate was stirred at 40° C. to 50° C. for about 2 hours, and then allowed to stand for cooling. The mixture was stirred at room temperature for 14 hours, and then stirred under ice-cooling for 2 hours. The precipitated crystals were collected by filtration to give the title compound as colorless crystals (87.5 g).

M.p.: 196–197° C.

Elementary Analysis:

Calculated for $C_{34}H_{44}ClNO_4 \cdot H_2O$; C: 63.79; H: 7.24; N: 10.94, Cl: 5.54.

Found; C: 63.89, H: 7.18, N: 10.82, Cl: 5.46;

Powder X-Ray Diffraction Data.

The X-ray diffraction pattern was measured by RINT2500V (manufactured by RIGAKU DENKI CORPORATION) using 1.541 Å of Cu—Kα. The diffraction angles (2θ) and the relative intensities of the main peaks in the X-ray diffraction pattern of the title crystalline compound are shown in Table 1, and the X-ray diffraction pattern thereof is shown in FIG. 1.

TABLE 1

| Diffraction Angles (2θ) (mean value) | Relative Intensity (%) (mean value) |
|---|---|
| 8.8 | 85 |
| 10.1 | 100 |
| 20.1 | 70 |
| 21.0 | 71 |

Stability Test

The crystals of N-[1-butyl-4-[3-[3-(hydroxy)propoxy]-phenyl]-1,2-dihydro-2-oxo-1,8-naphthyridin-3-yl]-N'-(2,6-diisopropyl-4-aminophenyl)urea hydrochloride monohydrate obtained in Example 1 and amorphous N-[1-butyl-4-[3-[3-(hydroxy)propoxy]phenyl]-1,2-dihydro-2-oxo-1,8-naphthyridin-3-yl]-N'-(2,6-diisopropyl-4-aminophenyl)urea hydrochloride were stored at a temperature of 60° C. under a relative humidity (R.H.) of 75% for 4 weeks. Then, the residual amount of the compound therein was quantitatively analyzed using High Performance Liquid Chromatography (HPLC). The results are shown in Table 2.

TABLE 2

| | HPLC Area Percentage (%) | |
|---|---|---|
| Storage period | Crystals | Amorphous |
| Initial value | 99.7 | 97.7 |
| 2 weeks | 99.6 | 94.6 |
| 4 weeks | 99.5 | 92.7 |

As is shown in Table 2, the crystals of N-[1-butyl-4-[3-[3-(hydroxy)propoxy]phenyl]-1,2-dihydro-2-oxo-1,8-naphthyridin-3-yl]-N'-(2,6-diisopropyl-4-aminophenyl)urea hydrochloride monohydrate are quite excellent in stability than amorphous N-[1-butyl-4-[3-[3-(hydroxy)propoxy]phenyl]-1,2-dihydro-2-oxo-1,8-naphthyridin-3-yl]-N'-(2,6-diisopropyl-4-aminophenyl)urea hydrochloride.

Industrial Applicability

The hydrate of the present invention is quite excellent in stability than the amorphous one, and when it is used in a pharmaceutical composition, there is less concern over the decomposition or the decrease in content thereof during the formulation procedures or storage period. Therefore, the hydrate of the present invention is more preferable for medicaments.

What is claimed is:

1. A monohydrate of N-[1-butyl-4-[3-[3-(hydroxyl)propoxy]-phenyl]-1,2-dihydro-2-oxo-1,8-naphthyridin-3-yl]-N'-(2,6-diisopropyl-4-aminophenyl)urea hydrochloride of the formula:

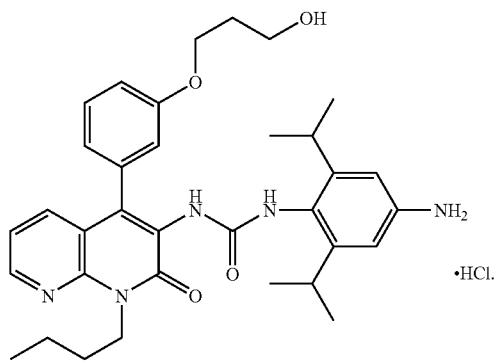

2. The compound according to claim 1, which has main peaks at the diffraction angles (2θ) of 8.8°, 10.1°, 20.1° and 21.0° in the powder X-ray diffraction pattern.

3. A pharmaceutical composition comprising the compound as set forth in claim 1 or 2.

4. A method for inhibiting an acyl-CoA: cholesterol acyl transferase (ACAT) in a patient, which comprises administering a therapeutically effective amount of the compound as set forth in claim 1 or 2 to a patient in need.

5. A method for treatment of hyperlipidemia or atherosclerosis, which comprises administering a therapeutically effective amount of the compound as set forth in claim 1 or 2 to a patient in need.

* * * * *